United States Patent [19]

Hoffmann et al.

[11] 4,166,850
[45] Sep. 4, 1979

[54] COMBATING PESTS WITH N-ACETYL-0-(2-CHLORO-1-FLUORO-ETHYL)-THIONOPHOSPHORIC (PHOSPHONIC) ACID ESTER-AMIDES

[75] Inventors: Hellmut Hoffmann, Wuppertal; Dieter Arlt; Ingeborg Hammann, both of Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 932,873

[22] Filed: Aug. 8, 1978

[30] Foreign Application Priority Data

Aug. 26, 1977 [DE] Fed. Rep. of Germany ....... 2738508

[51] Int. Cl.² ............................ A01N 9/36; C07F 9/22
[52] U.S. Cl. .................................... 424/220; 260/959; 260/971; 260/985
[58] Field of Search .......................... 260/959; 424/220

[56]  References Cited

U.S. PATENT DOCUMENTS 3,832,425  8/1974  Franke .......................... 260/959 OR Primary Examiner—Anton H. Sutto
Attorney, Agent, or Firm—Sprung, Felfe, Horn, Lynch & Kramer

[57]  ABSTRACT

N-Acetyl-0-(2-chloro-1-fluoro-ethyl)-thionophosphoric (phosphonic) acid ester-amides of the formula

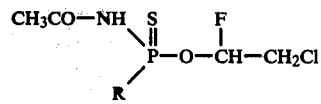

in which
R is alkyl or alkoxy, which possess arthropodicidal and nematicidal properties.

8 Claims, No Drawings

COMBATING PESTS WITH N-ACETYL-0-(2-CHLORO-1-FLUORO-ETHYL)-THIONOPHOSPHORIC (PHOSPHONIC) ACID ESTER-AMIDES

The present invention relates to and has for its objects the provision of particular new N-acetyl-O-(2-chloro-1-fluoroethyl)-thionophosphoric (phosphonic) acid ester-amides which possess arthropodicidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is already known that certain chlorine-substituted alkyl-phosphonic acid esters, for example O,O-dimethyl-2,2,2-trichloro-1-hydroxyethylphosphonic acid ester, are distinguished by an insecticidal and acaricidal activity (see U.S. Pat. No. 2,701,225).

The present invention now provides, as new compounds, the N-acetyl-O-(2-chloro-1-fluoro-ethyl)-thiono-phosphoric (phosphonic) acid ester-amides of the general formula

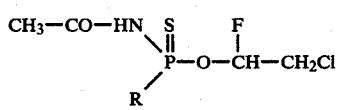

in which
R represents alkyl or alkoxy,

Preferably, R represents straight-chain or branched alkyl with 1 to 6 (especially 1 to 3) carbon atoms or straight-chain or branched alkoxy with 1 to 6 (especially 1 to 3) carbon atoms.

Surprisingly, the N-acetyl-O-(2-chloro-1-fluoroethyl)-thiono-phosphoric(phosphonic) acid ester-amides according to the invention exhibit a better insecticidal, acaricidal and nematicidal action than the corresponding chlorine-substituted alkylphosphonic acid esters of analogous structure and the same type of action. The products according to the present invention thus represent a true enrichment of the art.

The invention also provides a process for the preparation of an N-acetyl-O-(2-chloro-1-fluoro-ethyl)-thionophosphoric (phosphonic) acid ester-amide of the formula (I), in which an O-(2-chloro-1-fluoro-ethyl)-thiono-phosphoric(phosphonic) acid ester-amide of the general formula

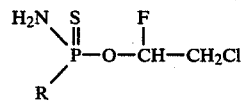

in which
R has the meaning stated above, is reacted with acetic anhydride, optionally in the presence of a solvent or diluent and optionally in the presence of an acid catalyst.

If, for example, O-iso-propyl-O-(2-chloro-1-fluoroethyl)-thionophosphoric acid diester-amide and acetic anhydride are used as the starting materials, the course of the reaction can be represented by the following equation:

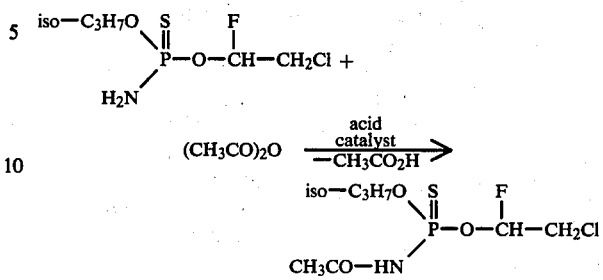

The O-(2-chloro-1-fluoro-ethyl)-thiono-phosphoric (phosphonic) acid ester-amides of the formula (II) to be used as starting materials are disclosed in U.S. Application Ser. No. 806,888, filed June 15, 977, now pending, and can be prepared by reacting O-(2-chloro-1-fluoroethyl)-thiono-phosphoric(phosphonic) acid ester halides of the general formula

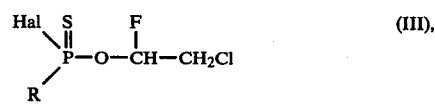

in which
Hal represents halogen, preferably chlorine, and
R has the meaning stated above, with ammonia, optionally in the presence of a solvent.

Examples of starting materials of the formula (II) which may be mentioned are: methane-, ethane- and n- or iso-propane-O-(2-chloro-1-fluoro-ethyl)-thionophosphonic acid ester-amide, and O-methyl-, O-ethyl- and O-n- or -iso-propyl-O-(2-chloro-1-fluoro-ethyl)-thionophosphoric acid diester-amide.

The O-(2-chloro-1-fluoro-ethyl)-thionophosphoric acid diester halides used as starting materials for the preparation of the compounds of the formula (II) can be prepared in a manner which is in itself known by reacting O-(2-chloro-1-fluoro-ethyl)-thionophosphoric acid ester dichloride with the corresponding alcohols.

The O-(2-chloro-1-fluoro-ethyl)-thionophosphoric acid ester dihalides to be used as starting materials and the O-(2-chloro-1-fluoro-ethyl)-thionophosphonic acid ester mono-halides can be obtained from the corresponding P=O compounds with alkane- or aryl-dithiophosphoric acid anhydrides, optionally mixed with phosphorus sulphochloride and optionally in the presence of a solvent, according to the following equation:

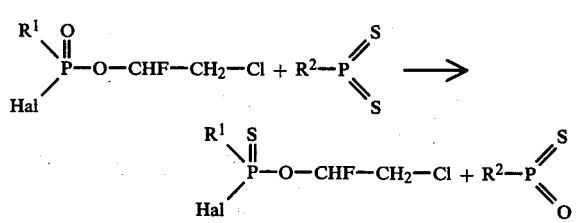

wherein
Hal has the meaning stated above,
$R^1$ represents Hal or alkyl and
$R^2$ represents alkyl or aryl.

Examples of the O-(2-chloro-1-fluoroethyl)-thionophosphoric acid ester dihalides and -thionophosphonic acid ester monohalides which may be mentioned are: methane-, ethane-, n-propane- and iso-propane-O-(2-chloro-1-fluoro-ethyl)-thionophosphonic acid ester chloride and O-(2-chloro-1-fluoro-ethyl)-thionophosphoric acid ester dichloride.

The O-(2-chloro-1-fluoro-ethyl)-phosphonic acid ester halides to be used here as starting materials and the O-(2-chloro-1-fluoro-ethyl)-phosphonic acid ester dihalides and O-alkyl-O-(2-chloro-1-fluoro-ethyl)-phosphoric acid diester halides can be prepared by a process which does not belong to the state of the art, by reacting a phosphoric (or phosphonic) acid ester and vinyl fluoride, simultaneously using a chlorinating agent, such as chlorine, at temperatures between −50° and +120° C., optionally in the presence of a Friedel-Crafts catalyst and optionally in the presence of a solvent, to give the corresponding O-(1-fluoro-2-chloroethyl)-phosphoric(-phosphonic) acid ester halides, according to the following equation:

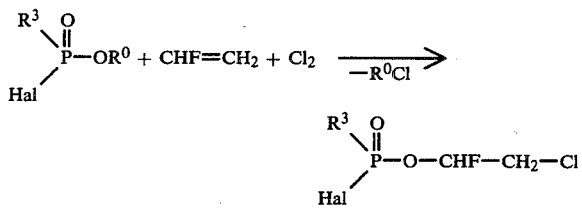

wherein

Hal has the meaning stated above, $R^3$ represents alkyl, alkoxy or Hal and $R°$ represents alkyl.

Examples of the O-(2-chloro-1-fluoro-ethyl)-phosphonic acid ester halides, O-(2-chloro-1-fluoro-ethyl)-phosphoric acid ester halides and O-alkyl-O-(2-chloro-1-fluoro-ethyl)-phosphoric acid diester halides which may be mentioned are: methane-, ethane-, n-propane- and iso-propane-O-(2-chloro-1-fluoro-ethyl)-phosphonic acid ester chloride, O-(2-chloro-1-fluoro-ethyl)-phosphoric acid ester dichloride and O-methyl-, O-ethyl-, O-n-propyl- and O-iso-propyl-O-(2-chloro-1-fluoro-ethyl)-phosphoric acid diester chloride.

The acetic anhydride which is also to be used as a starting material for the preparation of the compounds of the formula (I) is known.

The process for the preparation of the compounds according to the invention is preferably carried out also using a suitable solvent or diluent. Possible solvents or diluents are virtually all the inert organic solvents, especially aliphatic and aromatic, optionally chorinated hydrocarbons, such as benzene, toluene, xylene, benzine, methylene chloride, chloroform, carbon tetrachloride or chlorobenzene; ethers, for example diethyl ether, dibutyl ether and dioxane ketones, for example acetone, methyl ethyl ketone, methyl isopropyl ketone and methyl isobutyl ketone; and nitriles, such as acetonitrile and propionitrile. The starting material acetic anhydride can, however, be employed in excess and thus simultaneously serves as reactant and solvent. A few drops of sulphuric acid are preferably added as the catalyst.

The reaction temperature can be varied within a relatively wide range. In general, the reaction is carried out at from 30° to 100° C., preferably at from 45° to 75° C.

In general, the reaction is allowed to proceed under normal pressure.

For carrying out the reaction, both the reactants are introduced into a reaction vessel, the acetic anhydride preferably being employed in excess, and, after adding an acid catalyst, for example sulphuric acid, whereupon in exothermic reaction occurs, the mixture is subsequently reacted for a few hours. Thereafter, the reaction solution is taken up in an organic solvent and the organic phase is worked up in the customary manner by washing and drying and distilling off the solvent.

The new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. The refractive index is used for their characterization.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp.,

*Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., Niptus hololeucus, Gibbium psylloides, Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharanois* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Ripicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surfaceactive agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The compounds according to the present invention can also be used in the field of veterinary medicine, since they are also active against animal parasites.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids which comprises applying to said animals a compound according to the present invention, in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects and acarids by the application to said animals of a compound according to the present invention, in admixture with a diluent or carrier.

The preparation of the novel compounds is shown in the following illustrative examples:

EXAMPLE 1

(a) 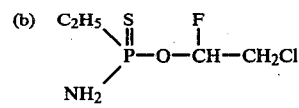

A slurry of 150 ml of toluene, 96 g (0.4 mol) of anisyldithiophosphoric acid anhydride and 84 g (0.4 mol) of O-(2-chloro-1-fluoro-ethyl)-ethane-phosphonic acid ester chloride was heated to 115°–120° C. for 2 hours, cooled and poured into 1 liter of ligroin. The mixture was filtered over kieselguhr, the solvent was evaporated off from the filtrate and the residue was distilled. 33 g (73% of theory) of O-(2-chloro-1-fluoro-ethyl)-thionoethane-phosphonic acid ester chloride with a boiling point of 82° C./2 mm Hg were obtained.

(b) 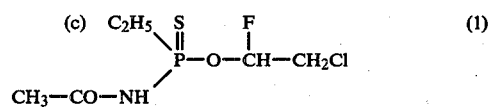

Ammonia was passed over a solution of 67.5 g (0.3 mol) of the O-(2-chloro-1-fluoro-ethyl)-thionoethanephosphonic acid ester chloride, prepared under (a), in 300 ml of acetonitrile, while stirring. The end of the reaction was recognized by the fact that the reaction mixture remained alkaline even after the stream of ammonia had been shut off. The reaction mixture was taken up in 500 ml of toluene and the organic phase was washed several times with water, dried over sodium sulphate and filtered. The toluene was distilled off in vacuo and the residue was subjected to incipient distillation using a mercury pump. 51 g (83% of theory) of O-(2-chloro-1-fluoro-ethyl)thionoethanephosphonic acid ester-amide having a refractive index $n_D^{24}$ of 1.5111 were obtained.

(c) 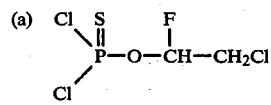 (1)

2 drops of pure, concentrated sulphuric acid were added to the mixture of 21 g (0.1 mol) of O-(2-chloro-1-fluoro-ethyl)-thionoethanephosphonic acid ester-amide and 11 g of acetic anhydride, whereupon the temperature rose to 55° C. The reaction mixture was left to stand overnight and taken up in toluene and the organic phase was washed with a bicarbonate solution until neutral. After drying the organic phase, the toluene was stripped off in vacuo and the residue was subjected to incipient distillation using a mercury pump. 18 g (73% of theory) of O-(2-chloro-1-fluoro-ethyl)-N-acetylthionoethanephosphonic acid esteramide having a refractive index $n_D^{24}$ of 1.5080 were obtained.

EXAMPLE 2:

(a) 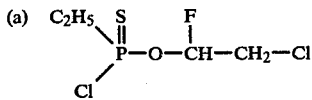

A mixture of 17 g of phosphorus sulphochloride, 12 g (0.05 mol) of O-(2-chloro-1-fluoro-ethyl)-phosphoric acid ester dichloride and 3 g of methanedithiophosphonic acid anhydride was heated to a temperature of 150° C. (externally) for 15 hours, cooled and diluted with 200 ml of ligroin. The mixture was filtered over kieselguhr, the solvent was evaporated off from the filtrate in vacuo and the residue was distilled. 7 g (61% of theory) of O-(2-chloro-1-fluoro-ethyl)-thionophosphoric acid ester dichloride, which was 90% pure according to the gas chromatogram and had a boiling point of 65° C./3 mm Hg, were obtained.

(b) 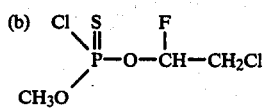

0.2 mol of sodium methylate in solution was added to a solution of 47 g (0.2 mol) of O-(2-chloro-1-fluoro-ethyl)-thionophosphoric acid ester dichloride in 300 ml of toluene, while cooling. The mixture was subsequently stirred at a temperature up to 10° C. for 30 minutes and washed twice with water. The organic layer was dried over sodium sulphate, the toluene was evaporated off under reduced pressure and the residue was distilled. O-Methyl-O-(2-chloro-1-fluoro-ethyl)-thionophosphoric acid diester chloride with a boiling point of 38°–42° C./0.01 mm Hg was obtained in 81% yield.

(c) 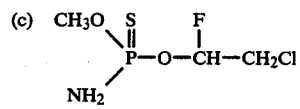

Ammonia was passed into a solution of 23 g (0.1 mol) of O-methyl-O-(2-chloro-1-fluoro-ethyl)-thionophosphoric acid diester chloride in 200 ml of acetonitrile at +20° C. until the reaction had ended. The reaction mixture was poured into water and the resulting mixture was taken up in toluene, the organic phase was washed with water and dried over sodium sulphate, the toluene was evaporated off and the residue was distilled under greatly reduced pressure. 16 g (77% of theory) of O-methyl-O-(2-chloro-1-fluoro-ethyl)-thionophosphoric acid diester-amide having a refractive index $n_D^{23}$ of 1.4930 were obtained.

(d) 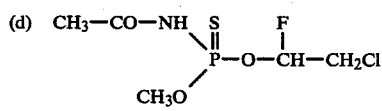 (2)

0.5 ml of pure, concentrated sulphuric acid was added to a solution of 20 ml of toluene, 21 g (0.1 mol) of O-methyl-O-(2-chloro-1-fluoro-ethyl)-thionophosphoric acid diester-amide and 11 g of acetic anhydride, while stirring, whereupon the temperature rose to 55° C. The reaction mixture was left to stand overnight and taken up in toluene and the organic phase was washed with a bicarbonate solution until neutral. After drying over sodium sulphate, the organic phase was filtered, the toluene was stripped off in vacuo and the residue was subjected to incipient distillation using a mercury pump. 16 g (64% of theory) of O-methyl-O-(2-chloro-1-fluoro-ethyl)-N-acetyl-thionophosphoric acid diester-amide having a refractive index of $n_D^{24}$ of 1.4959 were obtained.

The insecticidal, acaricidal and nematicidal activity of the compounds of this invention is illustrated by the following biotest Examples.

EXAMPLE 3

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined and the compound of Example 1 showed a good activity.

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined and the compound of Example 2 showed a good activity.

EXAMPLE 5

Critical concentration test/nematodes
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined.

In this test, for example, the compound of Example 1 showed a good activity.

EXAMPLE 6

Test with parasitic fly larvae
Emulsifier: 80 parts by weight of nonylphenol polyglycol ether To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*) were introduced into a test tube which contained approx. 2 ml of horse muscle. 0.5 ml of the preparation of active compound was applied to this horse meat. After 24 hours, the degree of destruction was determined.

In this test, for example, the compound of Example 2 showed a good activity.

It will be appreciated that the instant specification and examples are set forth by way of illustration and not limitation, and that various modifications and changes may be made without departing from the spirit and scope of the present invention.

What we claim is:

1. An N-acetyl-O-(2-chloro-1-fluoro-ethyl)-thionophosphoric (phosphonic) acid ester-amide of the formula

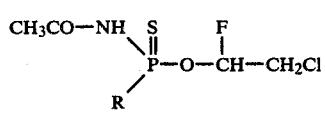

in which

R is alkyl or alkoxy.

2. A method of combating arthropods or nematodes which comprises applying to the arthropods or nematodes, or to a habitat thereof, an arthropodicidally or nematicidally effective amount of a compound according to claim 1.

3. A compound according to claim 1, in which R is alkyl with 1 to 6 carbon atoms or alkoxy with 1 to 6 carbon atoms.

4. A compound according to claim 1 wherein such compound is O-(2-chloro-1-fluoro-ethyl)-N-acetylthionoethanephosphonic acid ester-amide of the formula

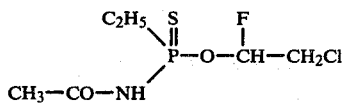

5. A compound according to claim 1, wherein such compound is O-methyl-O-(2-chloro-1-fluoro-ethyl)-N-acetyl-thionophosphoric acid diester-amide of the formula

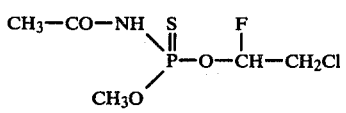

6. An arthropodicidal or nematicidal composition containing as active ingredient an arthropodicidally or nematicidally effective amount of a compound according to claim 1 in admixture with a diluent.

7. The method according to claim 2, wherein the compound is applied to a domesticated animal, thereby to protect the animal from ectoparasitical insects and acarids, and said compound is O-(2-chloro-1-fluoro-ethyl)-N-acetylthionoethanephosphonic acid ester-amide.

8. The method according to claim 2, wherein the compound is applied to a domesticated animal, thereby to protect the animal from ectoparasitical insects and acarids, and said compound is O-methyl-O-(2-chloro-1-fluoro-ethyl)-N-acetyl-thionophosphoric acid diester-amide.

* * * * *